United States Patent [19]

Wong

[11] 4,384,574
[45] May 24, 1983

[54] CONTROL APPARATUS

[76] Inventor: Albert Wong, 948 Micheltorena St., Los Angeles, Calif. 90026

[21] Appl. No.: 211,728

[22] Filed: Dec. 1, 1980

[51] Int. Cl.³ ............................................. A61F 13/00
[52] U.S. Cl. .................................... 128/133; 128/134; 119/152
[58] Field of Search ............................... 128/133, 134; 273/188 R, 188 A, 189 R, 189 A; 119/151, 152, 119/126, 127, 128

[56] References Cited

U.S. PATENT DOCUMENTS

| 1,301,349 | 4/1919 | Wylde | 119/128 |
| 1,817,845 | 8/1931 | Reichert | 119/128 |
| 1,845,338 | 2/1932 | Querna | 119/128 |
| 4,061,340 | 12/1977 | Husted | 128/134 |

FOREIGN PATENT DOCUMENTS 145881 of 1954 Sweden ................................ 119/126

Primary Examiner—Michael H. Thaler
Assistant Examiner—C. W. Shedd
Attorney, Agent, or Firm—Fulwider, Patton, Rieber, Lee & Utecht

[57] ABSTRACT

An apparatus used to control human beings through the application of localized pressure to their body and appendages. The claimed apparatus has a substantially straight, elongated first arm, and spaced therefrom and generally parallel thereto, a curved, elongated second arm. A member connects together one end of the first arm to the adjacent end of the second arm. The first arm extends beyond the second arm and a blunting element is fixedly secured to the free-end. The second arm has a curved midportion which curves downward and extends toward the first arm to a distance from the first arm sufficient to receive an appendage. An upwardly curved end portion of the second arm connects the curved midportion to the connecting member, and attached to the end of the curved midportion remote from the connecting member is an upwardly curved free-end portion. The free-end portion has a free-end section which extends in a direction generally away from the connecting member and downward toward the first arm to a distance from the first arm greater than the distance between the curved midportion and the first arm. The apparatus is formed as a unitary structure from a continuous band of flat material.

7 Claims, 13 Drawing Figures

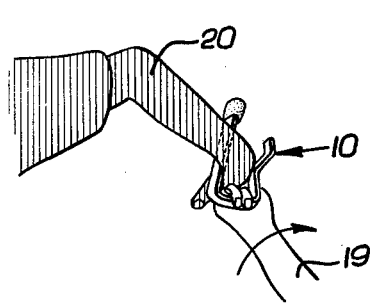
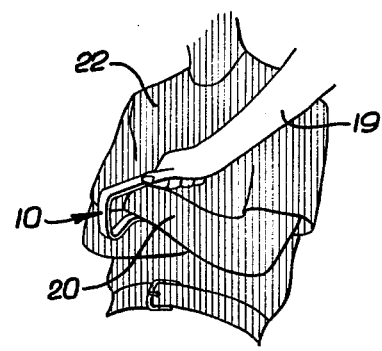
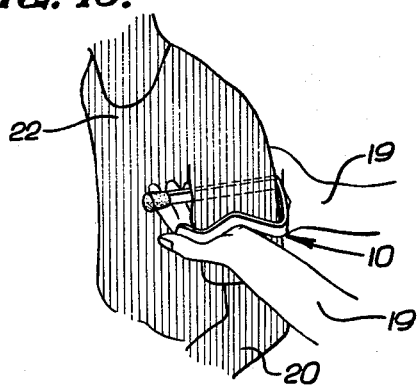
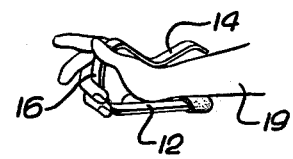
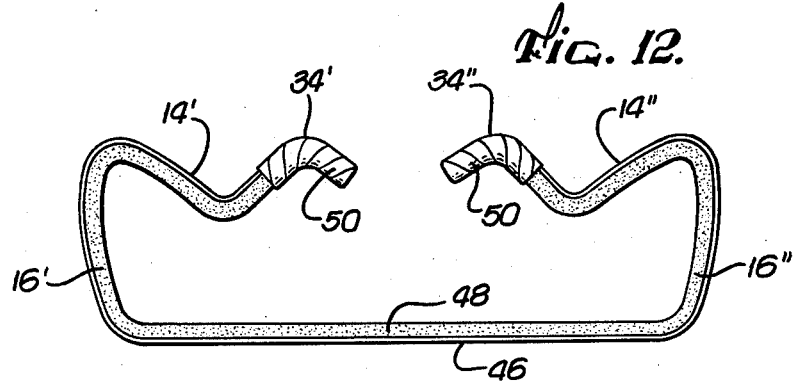
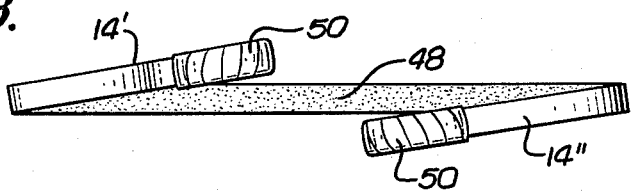

CONTROL APPARATUS

BACKGROUND OF THE INVENTION

The present invention relates generally to mechanical control devices and, more particularly, to a apparatus for the control of human beings utilizing physical pressure.

In some situations, policemen and others must use physical force to cause individuals who will not respond to oral commands to act in a desired way. In the past, when an unarmed individual passively or forcefully refused to respond, various holds were used to control the uncooperative individual. Arm and neck locks, and the like, applied with or without the aid of a night stick or other device, are common holds which utilize the application of physical pain for control. Persons with training in certain martial arts, such as jujitsu, can use much more sophisticated holds, some of which are designed to apply localized pressure to various parts of the body for the purpose of control.

Many of these holds, however, require a level of physical strength not had by smaller persons, and the use of both hands. Other, more sophisticated holds, require extensive training not generally provided to policemen. Furthermore, some holds are dangerous to the individual being controlled, particularly the neck lock, which can result in asphyxiation if too great a force is applied. In certain situations, such as when the individual who does not respond is seated within a car, or has both arms crossed and held tightly to his chest, many holds cannot be used because of the difficulty of placing the individual in the hold.

It will therefore be appreciated that there is a significant need for an effective, mechanical control apparatus which can be used to control human beings. Ideally, such a apparatus should permit the user to inflict selectively varying amounts of physical pain to a subject in a manner that does not wound or endanger the life of the subject, and be easily operated with one or two hands. Operation of the apparatus should not require great physical strength or extensive training, and the apparatus should be portable and inexpensive. The present invention fulfills this need, and further provides other related advantages.

SUMMARY OF THE INVENTION

The present invention resides in an apparatus for the control of human beings by the application of localized pressure to their body and appendages, the apparatus having a first arm, a second arm spaced from and generally parallel to the first arm, and a connecting member connecting together one end of the first arm to the adjacent end of the second arm. The second arm has a first portion extending toward the first arm to a distance from the first arm sufficient to receive the appendage to which the pressure is to be applied, and an end portion remote from the connecting which extends toward the first arm to a distance from the first arm at least as great as the distance between the first portion of the second arm and the first arm. The first arm extends beyond the second arm in a direction away from the connecting member, and a blunting element is fixedly secured to the end of the first arm remote from the connecting member to permit the application of pressure to the body of a subject individual.

More specifically, in the presently preferred embodiment of the invention, the first arm is substantially straight, and the first portion of the second arm is downwardly curved toward the first arm. The second arm has an upwardly curved portion connecting the first portion to the connecting member. The apparatus is a unitary structure with the first and second arms having narrow, longitudinal sides, and is entirely covered with a soft, non-slip coating.

The first and second arms and connecting member have sufficient strength and stiffness to resist bending under the normal forces exerted during use of the apparatus, and are bendable to hold the first arm at a preselected distance from the second arm. The first and second arms and connecting member also have sufficient flexibility and resiliency to permit movement of the first arm toward the second arm during use of the apparatus by a clamping action, without significantly deforming the shape of the apparatus.

In another of the presently preferred embodiment of the invention, the apparatus includes a pair of arms, each shaped substantially identical to the first arm of the first described embodiment, which are spaced from and generally parallel to a base having first and second end sections and an intermediate section. A first connecting member connects the first end section of the base to the adjacent end of one arm, and a second connecting member connects the second end section of the base to the adjacent end of the other arm.

Other features and advantages of the invention will become apparent from the following detailed description, taken in conjunction with accompanying drawings.

BRIEF DESCRIPTION OF THE DRAWINGS

FIG. 8 is a reduced scale, perspective view of the apparatus shown in FIG. 1 being operated with one hand by a twisting action on the wrist of a subject;

FIG. 9 is a reduced scale, perspective view of the apparatus shown in FIG. 1 being inserted between the crossed arms of a subject;

FIG. 10 is a reduced scale, perspective view of the apparatus shown in FIG. 1 being operated with two hand by a clamping action;

FIG. 11 is a reduced scale, perspective view of the apparatus shown in FIG. 1 being held in readiness in a manner protecting the user's wrist;

FIG. 12 is a front elevational view of an alternative embodiment of the apparatus shown in FIG. 1; and FIG. 13 is a plan view of the apparatus shown in FIG. 12.

DETAILED DESCRIPTION

Figure 1:
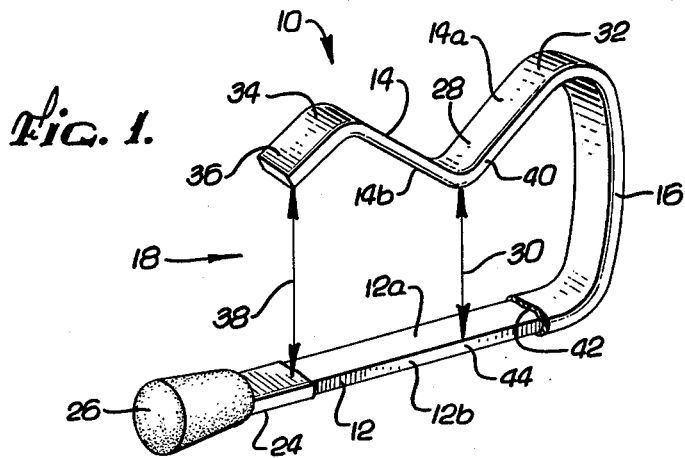
FIG. 1 is a perspective view of a control apparatus embodying the present invention.

As shown in the drawings for purposes of illustration, the present invention is embodied in an apparatus, indicated generally by reference numeral 10, used to control human beings through the application of localized physical pressure to their body and appendages.

In accordance with the invention, the apparatus 10 has a substantially straight, elongated first arm 12, and spaced therefrom and generally parallel thereto, a curved, elongated second arm 14. A connecting member 16 connects together one end of the first arm 12 to the adjacent end of the second arm 14. The free-ends of the first and second arms remote from the connecting member form an opening 18, through which an appendage 20 of a subject individual 22 passes upon entering the apparatus. The apparatus 10 provides a mechanical control device of inexpensive construction that is effective, but yet is easy to use and does not require great strength or extensive training on the part of a user 19.

More specifically, the first arm 12 has a free-end portion 24, remote from the connecting member 16, which extends beyond the second arm in a direction away from the connecting member. Fixedly secured to the end of the free-end portion 24 of the first arm 12 is a blunting element 26.

The second arm 14 has a curved midportion 28, located along its longitudinal midsection, which curves downward and extends toward the first arm 12 to a distance 30 from the first arm sufficient to receive the appendage 20 of the subject individual 22 who is to be controlled through use of the apparatus 10. An upwardly curved end portion 32 of the second arm 14 connects the curved midportion 28 to the connecting member 16.

Attached to the curved midportion 28, at its end remote from the connecting member 16, is an upwardly curved free-end portion 34 of the second arm 14. The free-end portion 34 has a free-end section 36 extending in a direction generally away from the connecting member 16 and toward the first arm 12. The free-end section 36 extends downward to a distance 38 from the first arm which is greater that the distance between the curved midportion 28 and the first arm 12, to make the opening 18 sufficiently wide for easy passage of an appendage 20 into the apparatus 10.

In the presently preferred embodiment of the invention, the first arm 12, second arm 14 and connecting member 16 of the apparatus 10 are formed from a continuous band of thin, flat material. The first arm 12 has top and bottom flat faces 12a and 12b, respectively, and the second arm 14 has top and bottom flat faces 14a and 14b, respectively. The bottom face 12b of the first arm and the top face 14a of the second arm face toward each other and are substantially parallel.

The localized physical pressure which produces the physical pain upon which the apparatus relies to achieve control of the subject individual 22, may be applied by placing the appendage 20 between the first and second arms 12 and 14, and twisting the apparatus about an axis generally parallel to and midway between the first and second arms to engage the appendage. The second arm 14 has narrow, rounded longitudinal sides 40 which extend along and are contiguous with the longitudinal edges of the arm's top and bottom faces 14a and 14b. The twisting action places one of the narrow sides 40 into contact with the appendage, and applies physical pressure to the surface area of the appendage contacted by the apparatus.

Because of the localized nature of the pressure, only a relatively small force is needed to cause the subject individual 22 to experience a level of pain beyond the threshold of tolerance and, consequently, to produce the submission of most people. While capable of inflicting great pain, the rounded shape of the narrow sides 40 prevents cutting of the appendage skin, and the apparatus 10 causes no damage to the individual except for minor bruises. The chance of damage to the appendage skin is further reduced by completely covering the apparatus 10 with a soft, non-slip coating 42, such as rubber. The non-slip coating 42 also inhibits slippage of the apparatus 10 in the hands of the user 19, and slippage of the appendage 20 of the subject individual 22 out of the apparatus.

When the apparatus 10 is operated, the first arm 12 serves to provide a counterforce permitting the application of pressure to the appendage 20 by the second arm 14. The first arm 12, however, may also be constructed with narrow, rounded longitudinal sides 44 extending along and contiguous with the longitudinal edges of the arm's top and bottom faces 12a and 12b, similar to the narrow sides 40 of the second arm 14. With such construction, upon twisting of the apparatus 10 both a narrow side 44 of the first arm 12 and a narrow side 40 of the second arm 14 apply localized pressure to the appendage surface area each contacts, thereby increasing the effectiveness of the apparatus 10.

The user 19 of the apparatus 10 can quickly and easily vary the degree and duration of the pain inflicted by increasing or decreasing the force used to twist the apparatus. The capability of selective varying the pain permits the user 19 to respond almost instantaneously to any belligerent or non-cooperative movement of the subject individual 22, and to inflict only so much pain as is mandatory to keep the subject responding to the oral commands of the user.

Figure 2:
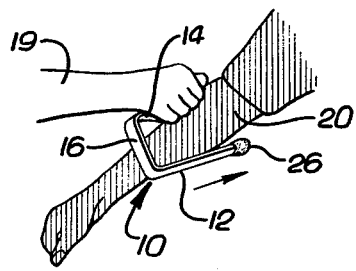
FIG. 2 is a reduced scale, perspective view of the apparatus shown in FIG. 1 being positioned on an appendage of a subject individual.
Figure 3:
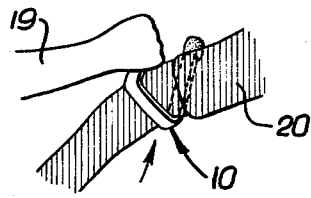
FIG. 3 is a perspective view of the apparatus shown being positioned in FIG. 2, with the subject's appendage fully within the apparatus.
Figure 4:
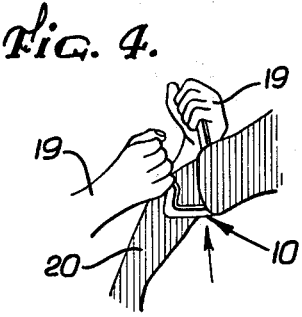
FIG. 4 is a perspective view of the apparatus shown positioned in FIG. 3 being operated with two hands by a twisting action.

The twisting action may be applied by grasping the connecting member 16 with one hand (see FIG. 7), or by grasping in one hand the free-end portion 24 of the first arm 12 and in a second hand the free-end portion 34 of the second arm 14 (see FIG. 4). A method of placing the appendage 20 within the apparatus 10 in preparation for its operation with two hands is shown by sequential illustrations FIGS. 2 and 3. The user 19 grasps the apparatus 10 in one hand by the free-end portion 34, resting the thumb of the hand over the free-end section 36 for greater control, with the first arm 12 positioned toward the appendage 20. In a swinging motion, the apparatus 10 is moved toward the appendage 20 so that the appendage passes through the opening 18 between the first and second arms 12 and 14. Once the appendage is completely within the apparatus, the second hand of the user grasps the free-end portion 24 of the first arm, and commences the twisting action, as shown in FIG. 4.

Figure 7:
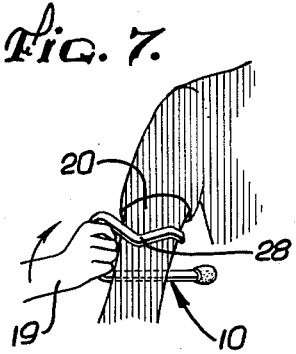
FIG. 7 is a reduced scale, perspective view of the apparatus shown in FIG. 1 being operated with one hand by a twisting action on the forearm of a subject.

The apparatus 10 may be used to apply pressure to the wrist, upper arm or lower arm of the subject individual 22. As shown in FIGS. 7 and 8, the curved midportion 28 of the second arm 14 can be positioned immediately over the appendage 20 and the apparatus 10 twisted to bring the midportion into contact with the appendage. Alternately, as shown in FIG. 4, the appendage 20 can be positioned within the apparatus 10, abutting the connecting member 16, so that when the apparatus is twisted the curved end portion 32 of the second arm 14 contacts the appendage.

In the presently preferred embodiment of the invention, the first arm 12, and the second arm 14 and the connecting member 16 are constructed of a material, such as galvanized steel 10–40, having sufficient strength and stiffness to resist bending under normal forces exerted on the apparatus 10 during use, but yet being bendable by the user 19 to place and hold the first arm at a preselected distance from the second arm. With such construction, one size apparatus 10 can accommodate the narrow wrist or the thicker upper arm of the subject individual 22, and can be used on subjects with varying sizes of appendages by merely bending the first and second arms closer together or farther apart.

Figure 6:
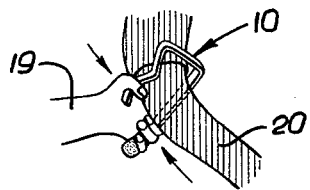
FIG. 6 is a reduced scale, perspective view of the apparatus shown in FIG. 1 being operated by a clamping action.

Use of a flexible but resilient material for the first and second arms 12 and 14 and the connecting member 16 permits operation of the apparatus 10 to apply localized physical pressure in a manner alternative to that described above. The appendage 20 of the subject individual 22 is clamped between the curved midportion 28 of the second arm and the first arm, by movement of the first and second arms toward each other. The clamped action can be conveniently applied (see FIGS. 6 and 10) by grasping in one hand the free-end portion 24 of the first arm 12 and the free-end portion 34 of the second arm 14, and squeezing. As with the twisting action, only a relatively small force is needed to cause enough pain to produce the submission of most people.

As shown in FIG. 9, the curved and slender shape of the free-end portion 34 of the second arm 14 allows it to be easily inserted between the crossed arms of the subject individual 22 to place the appendage 20 of the subject within the apparatus 10. In other situations, where the appendage of the subject individual is being held at a distance from his body, such as in FIG. 7, the user 19 may simply grasp the apparatus 10 by the connecting member 16 and thrust it forward and around the appendage.

To conceal the purpose for which the apparatus 10 is intended to be used until the moment just before it must be positioned for a thrust, the apparatus may be held by the connecting member 16 with the first and second arms 12 and 14 extending in a reverse direction, pointing toward the user 19, as shown in FIG. 11. In this position, the apparatus can be used as a shield to block blows to the hand and wrist of the user 19, and when necessary, quickly flipped around, rotating about an axis passing longitudinally through the connecting member 16, to point in the direction of the subject individual 22.

Figure 5:
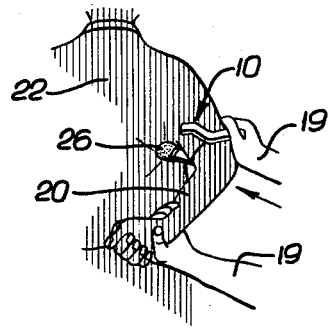
FIG. 5 is a reduced scale, perspective view of the apparatus shown in FIG. 1 being operated on the forearm of a subject, with a blunt force being applied to the body of the subject.

Another use for the apparatus 10 is as a probe (see FIG. 5). The blunting element 26 secured to the free-end portion 24 of the first arm 12 may be pushed with selectively varying force against the body of the subject individual 22 to apply an additional pressure point to encourage his locomotion, while at the same time a twisting action applies pressure on his appendage.

A second embodiment of the apparatus 10', illustrated in FIGS. 12 and 13, is similar in construction and operation to the previously described apparatus 10, but utilizes a pair of curved, elongated arms 14' and 14" which are spaced from and generally parallel to a substantially straight, elongated base 46. A connecting member 16' connects one distal end of the base 46 to the adjacent end of the arm 14', and a connecting member 16" connects to a second distal end of the base to the adjacent end of the arm 14". The arms 14' and 14" have free-end portions 34' and 34", respectively, which generally extend downward and toward each other, and are remote from their respective connecting members 16' and 16". The curvature of the arms 14' and 14" is substantial identical to that of the second arm 14 of the first embodiment of the invention. As shown in FIG. 14, the arms 14' and 14" are not precisely coaxial, but each is skewed to opposite sides of the base 46.

In the second embodiment of the invention, the interior surface of the apparatus 10' is lined with a soft foam 48, and the free-end portions 34' and 34" of the arms 14' and 14" are provided with a protective coating 50. Alternatively, as in the first embodiment, the entire apparatus may be completely covered with a soft, non-slip coating, such as rubber.

From the foregoing, it will be appreciated that the invention, as described herein for purposes of illustration, provides an apparatus which may be safely and effectively used for the control of human beings through the application of localized physical pressure to their body and appendages. The pain inflicted may be selectively varied, and its infliction does not require great physical strength on the part of the user. The apparatus of the invention is not difficult to operate with a minimum of training, and is easily carried and inexpensive to manufacture. It will also be appreciated that, although specific embodiments of the invention have been described herein for purposes of illustration, various modifications may be made without departing from the spirit and scope of the invention. Accordingly, the invention is not limited except as by the appended claims.

I claim:

1. An apparatus for the control of a human being by the selective application of localized pressure to an appendage, comprising a generally U-shaped member of substantially rectangular stock having a cross section defined by opposing relatively wide surfaces and opposing relatively narrow surfaces, said U-shaped member having first and second arms with a connecting member therebetween, said relatively wide surfaces of said first and second arms being generally in opposing relation, said first and second arms extending in generally parallel directions, said first arm being substantially straight and extending beyond said second arm, said second arm being corrugated to define two crests and a single valley therebetween with said valley opening in a direction away from said first arm, said first and second arms being sufficiently spaced apart to receive therebetween said appendage and coact to apply localized pressure to said appendage by twisting said apparatus or squeezing together said first arm relative to said second arm with said appendage therebetween.

2. The apparatus of claim 1, wherein said second arm has an end portion, remote from said connecting member, opposing and angularly extending toward, but spaced from said first arm a distance sufficient to receive said appendage.

3. The apparatus of claim 1, further including a blunting element fixedly secured to an end of said first arm remote from said connecting member.

4. The apparatus of claim 1, wherein said first and second arms are covered with a soft, non-slip coating.

5. The apparatus of claim 1, wherein said first arm, said second arm and said connecting member are a unitary structure.

6. The apparatus of claim 5, wherein said first and second arms and said connecting member have sufficient strength and stiffness to resist twisting under normal forces exerted during use of the apparatus, but are bendable to adjustably hold said first arm at a preselected distance from said second arm.

7. The apparatus of claim 5, wherein said first and second arms and said connecting member have sufficient flexibility and resiliency to permit movement of said first arm toward said second arm under normal forces exerted during use of the apparatus without significant permanent deformation of the shape of the apparatus.

* * * * *